(12) United States Patent
Small (10) Patent No.: US 7,591,269 B2
(45) Date of Patent: Sep. 22, 2009

(54) MEDICAL PROCEDURE DRAPE (76) Inventor: Thomas J. Small, 485 Augusta Ct., Franklin, IN (US) 46131

( * ) Notice: Subject to any disclaimer, the term of this patent is extended or adjusted under 35 U.S.C. 154(b) by 417 days.

(21) Appl. No.: 11/118,643

(22) Filed: Apr. 29, 2005

(65) Prior Publication Data
US 2006/0243285 A1    Nov. 2, 2006

(51) Int. Cl.
A61B 19/00    (2006.01)
(52) U.S. Cl. .................................................. 128/849
(58) Field of Classification Search ............ 128/847, 128/851–855, 849
See application file for complete search history.

(56) References Cited
U.S. PATENT DOCUMENTS 4,476,860 A    10/1984  Collins et al.
4,508,526 A *   4/1985  Dutcher ..................... 493/346
4,739,753 A *   4/1988  Brehm .................. 128/200.24
4,936,318 A *   6/1990  Schoolman ................ 128/847
4,946,125 A *   8/1990  McCarty .................. 248/316.7
5,386,835 A    2/1995  Elphick et al.
5,445,165 A *   8/1995  Fenwick .................... 128/849
5,471,999 A   12/1995  Mills
5,765,566 A    6/1998  Rothrum
5,960,794 A   10/1999  Shaw
5,975,082 A * 11/1999  Dowdy ..................... 128/849
5,988,172 A   11/1999  Sosebee
6,357,445 B1   3/2002  Shaw
6,871,651 B2 *  3/2005  Lanier ..................... 128/852
6,938,628 B2 *  9/2005  Cooley .................... 134/195
2004/0231677 A1 11/2004  Wallin

* cited by examiner

Primary Examiner—Patricia Bianco
Assistant Examiner—Camtu T Nguyen
(74) Attorney, Agent, or Firm—Bose McKinney & Evans LLP (57) ABSTRACT A medical procedure drape for use during a medical procedure such as a colonoscopy. The medical procedure drape includes a cover and a barrier.

15 Claims, 10 Drawing Sheets

MEDICAL PROCEDURE DRAPE

FIELD OF THE INVENTION

This invention relates generally to a method and apparatus for use during a medical procedure and more particularly to a medical procedure drape for use during a medical procedure including colonoscopy, sigmoidoscopy, proctoscopy, with or without biopsy, polypectomy, or endoscopic photography.

BACKGROUND AND SUMMARY

Colonoscopy is a medical procedure or test whereby a physician or other caregiver uses a fiberoptic device to visually examine a patient's colon and rectum. Typically, a colonoscopy may be performed to assess the anatomy of the lining of the colon and rectum. A colonoscopy may detect the presence of polyps or other cancerous or precancerous tissue. In addition, information related to other diagnoses such as terminal ileitis or colitis may be ascertained during a colonoscopy.

Flexible fiberoptic colonoscopy first appeared as a diagnostic and therapeutic procedure in the mid 1970s. It has become an effective tool for evaluating the colonic mucosa and diagnosing and treating diseases of the large intestine. Screening colonoscopy has become a mainstay of appropriate medical care and the removal of pre-malignant polyps has reduced the incidence of colon cancer. Patients scheduled for colonoscopy engage in a laxative preparation usually done on the day prior to the examination or procedure. The patient may be brought to an outpatient facility and examined by a physician and evaluated by the nursing staff. Pre-operative vital signs are taken and an intravenous site is secured. The patient is moved to the endoscope suite where he is or she is placed in the lateral position, lying on the left side, on a patient cart, bed, or stretcher. Cardiac and pulmonary systems are monitored closely.

Typically, the patient is positioned with the patient's back relatively straight and parallel to the longitudinal direction of the cart and close to the edge with the hips flexed approximately 45°. This places the lower legs in line with the longitudinal axis of the patient cart. The procedure may be completed either under conscious sedation or a general anesthetic. Once the patient is appropriately anesthetized or sedated, blankets are removed and the patient is prepared for the colonoscopy. Once the procedure is completed, the patient is cleansed and removed to another room for recovery.

In accordance with one aspect of the present invention, there is provided a medical procedure drape for use during a medical procedure performed on a patient supported by a patient support including a cover and barrier. The cover includes a first portion to superimpose at least a portion of a patient and a second portion to superimpose at least a portion of the patient support, and a barrier, disposed adjacent the cover. The barrier extends above the patient support surface.

In another aspect of the invention there is provided a method of reducing contamination of a physician during a medical procedure performed on a patient supported on a patient support. The method includes the steps of providing a cover having a first side and a second side, providing a barrier, coupling the barrier to the patient support, and covering the patient support and the barrier with the cover.

DETAILED DESCRIPTION OF THE DRAWINGS

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
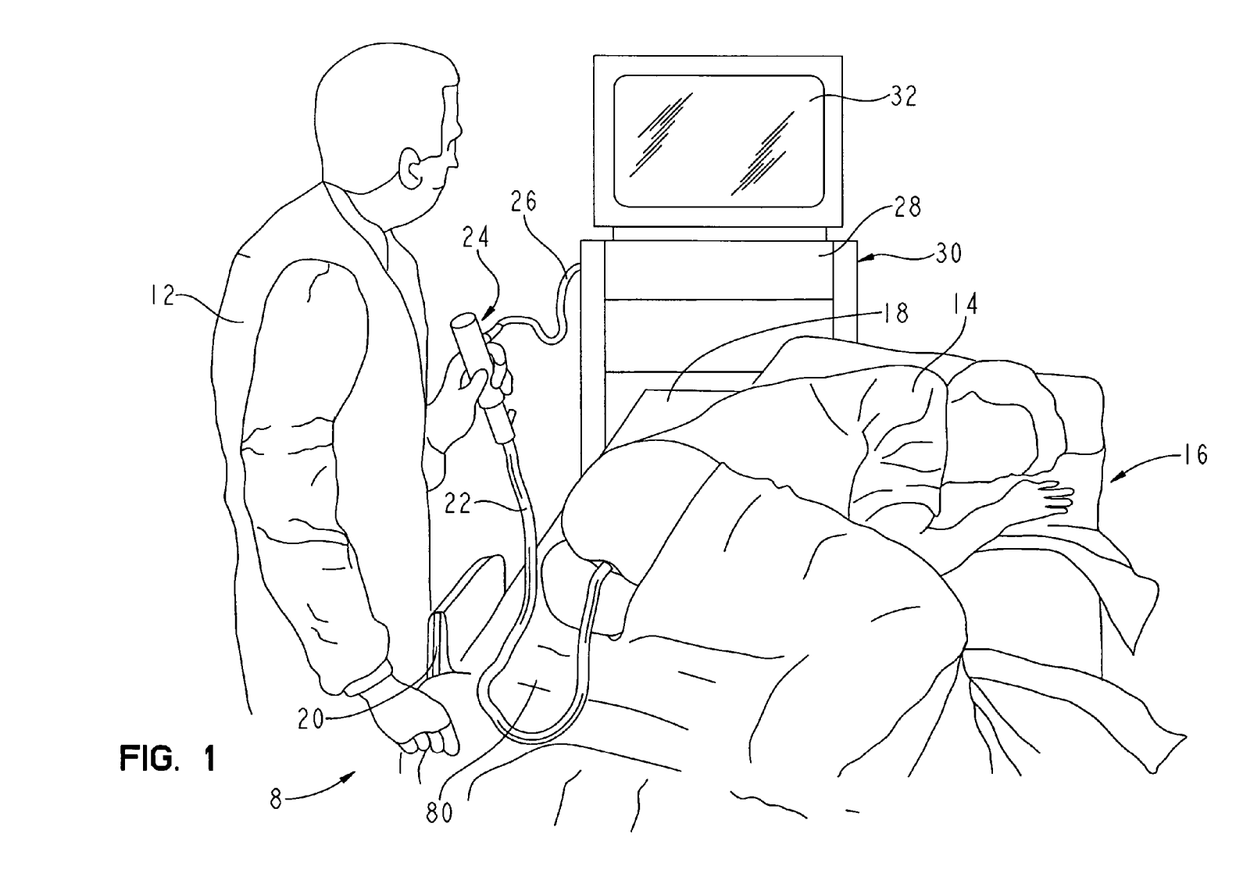
FIG. 1 is a perspective view of a patient undergoing a colonoscopy performed by a physician using a colonoscope and a medical procedure drape.

Referring now to FIG. 1, there is shown a medical procedure drape 8, including a cover 10 for assisting a physician 12, endoscopist, or other caregiver, when performing a colonoscopy or other endoscopic procedure on a patient 14. During the procedure, the patient 14 is anesthetized while lying on a patient supporting device 16, which may include a bed, cart, or stretcher. The patient supporting device 16 may include a mattress 18 upon which the patient 14 lies. In FIG. 1, the patient 14 is shown lying at an angle for ease of illustration. As previously described, the patient would typically lie with the patient's back longitudinally aligned with the long axis of the patient support device 16. The endoscopist has removed his right hand from the colonoscope so as to demonstrate the detail of the position of the procedure drape, the barrier, the colonoscope, and the patient.

To perform a colonoscopy or other medical procedure using the present invention, the cover 10 is laid upon or superimposes the patient's legs whereby a portion of the medical cover 10 covers a barrier 20. The physician 12 inserts a flexible tube 22 of a fiberoptic flexible colonoscope 24 into the patient's colon. The flexible tube includes fiberoptic cable including an air supply for inflating the colon and a light for examining the mucosa therein. A communication cable 26 is coupled to medical equipment 28 supported by an equipment cart 30. The medical equipment 28 includes signal processing equipment and other control devices for supplying the camera signal to a video monitor 32.

Figure 2:
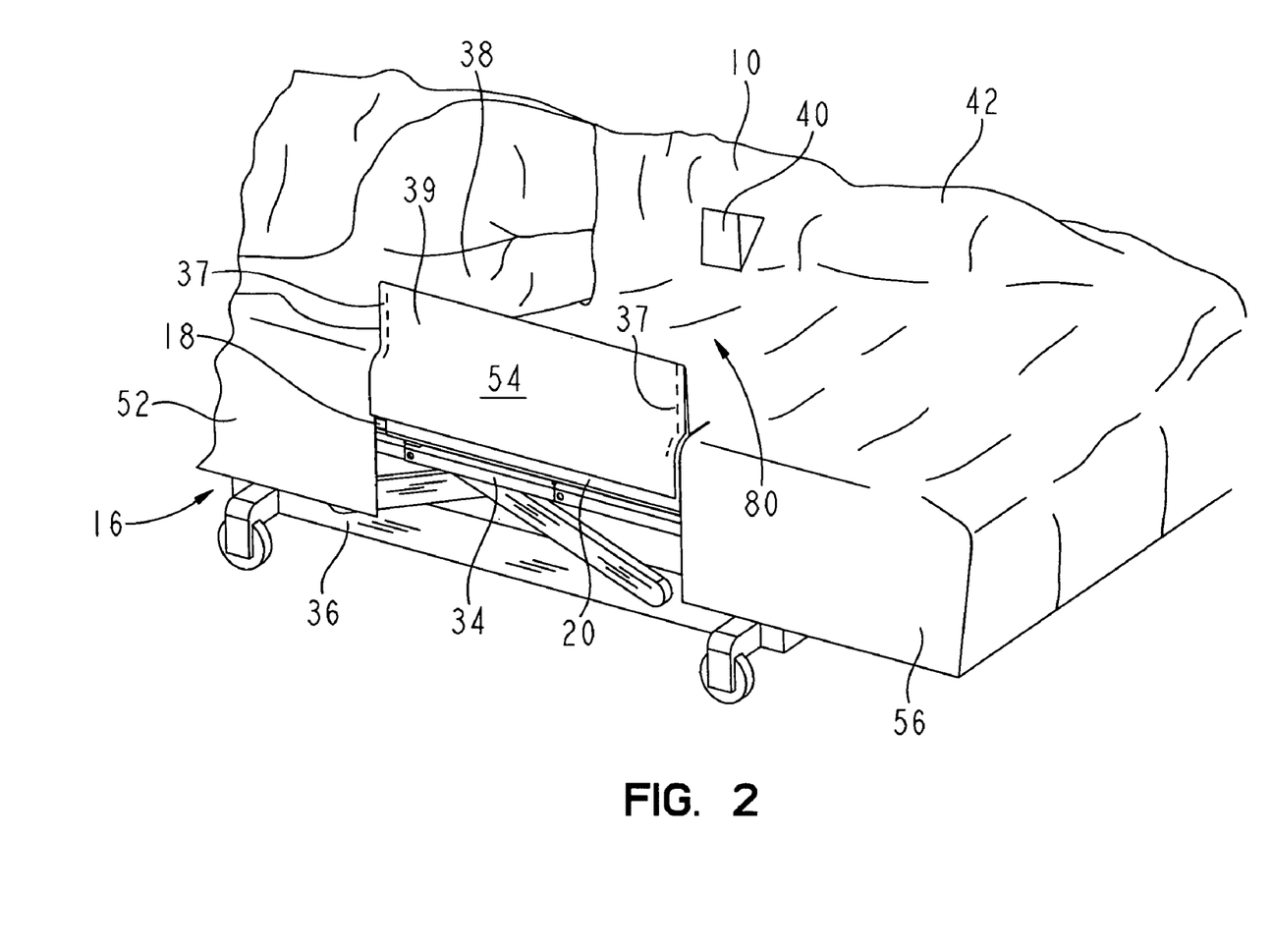
FIG. 2 is a perspective view of the patient of FIG. 1, including the medical procedure drape having a barrier covered with a cover.
Figure 6:
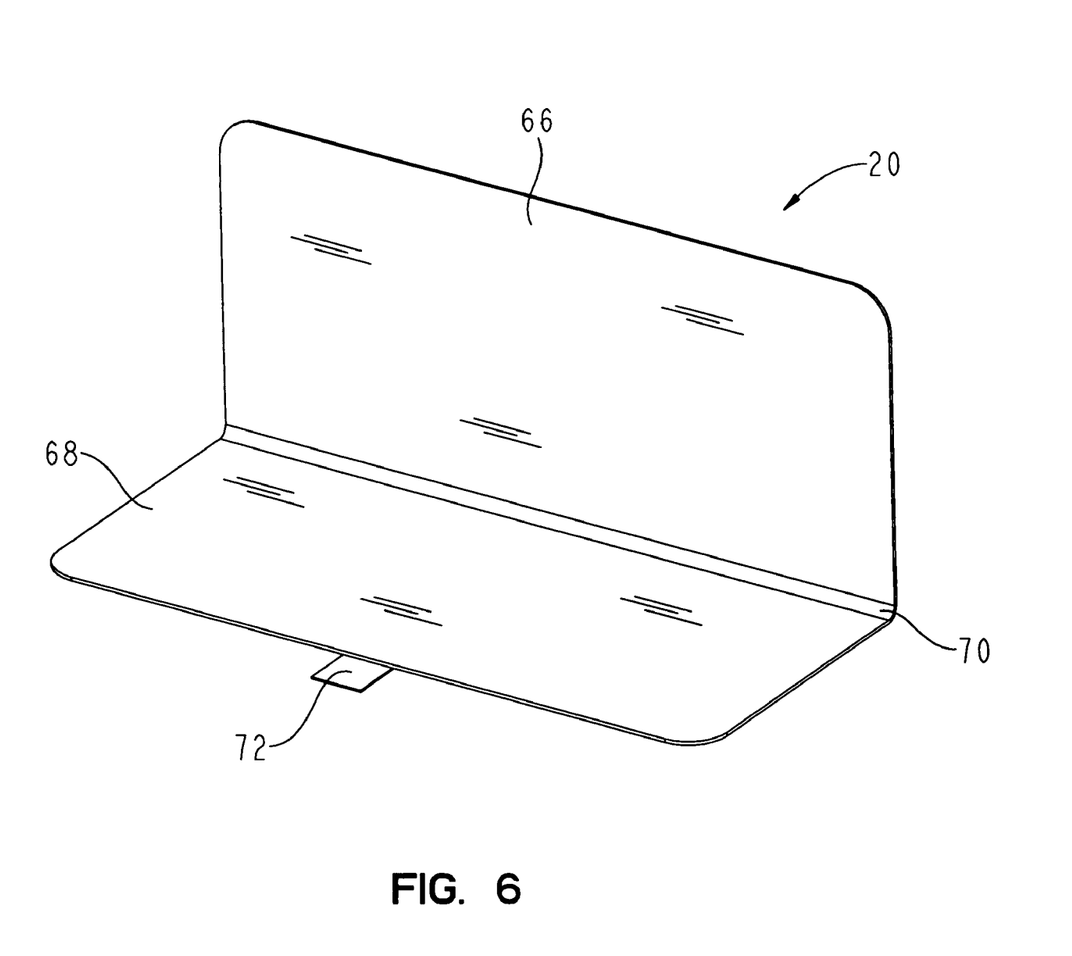
FIG. 6 is a perspective view of the barrier of the present invention.
Figure 7:
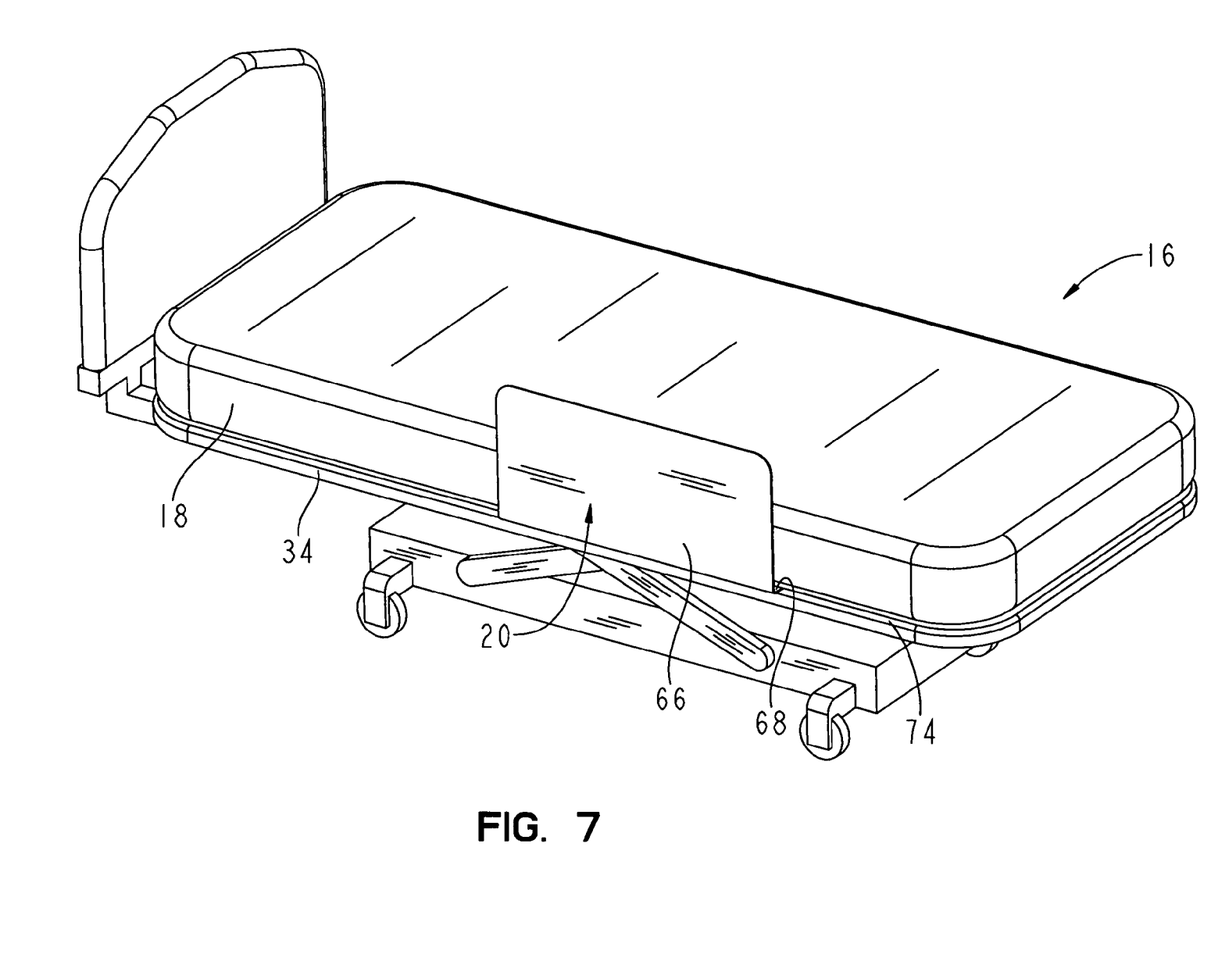
FIG. 7 is a perspective view of a patient support including the barrier positioned at the patient support.

FIG. 2 is a perspective view of FIG. 1 including the cover 10, the barrier 20, and the mattress 18. Once the patient is under conscious sedation or general anesthetic, blankets on the patient are removed from the lower portion of the patient, and the cover 10 is applied to the patient. The cover 10 covers the lower portion of the patient and may cover a lower portion of the patient support device 16. In addition, the barrier 20 seen also in FIGS. 6 and 7, is positioned at the patient support. A portion of the barrier 20 is located between the mattress 18 and a deck 34 coupled to a frame 36 of the patient support device 16. A portion of the cover 10 covers the barrier 20. The cover 10 may be glued, stitched, adhered, or held at the lines 37 to form a pocket 39 which fits over the barrier 20.

Another portion of the cover is positioned beneath the patient's left hip 38. In addition, the cover 10 may include a pocket or holder 40 coupled to the cover 10 which may hold medical procedure devices including tools, swabs, gauze squares, or surgical wipes.

Figure 3:
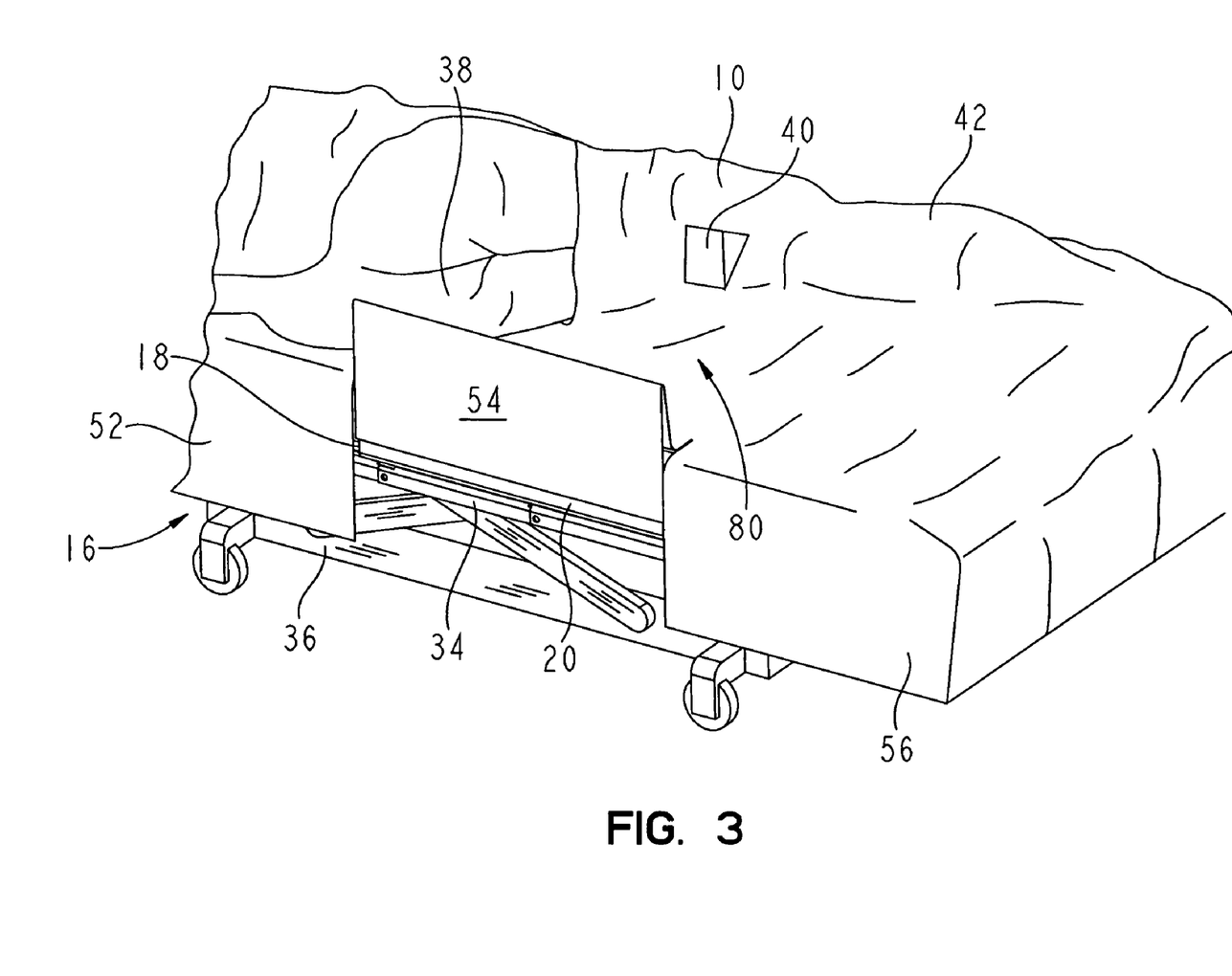
FIG. 3 is a perspective view of the patient of FIG. 1, including another embodiment of the medical procedure drape.

FIG. 3 illustrates another embodiment of the medical procedure drape 10. The portion covering the barrier 20 does not include a preformed pocket to cover the barrier, but instead hangs loosely over the barrier.

Figure 4:
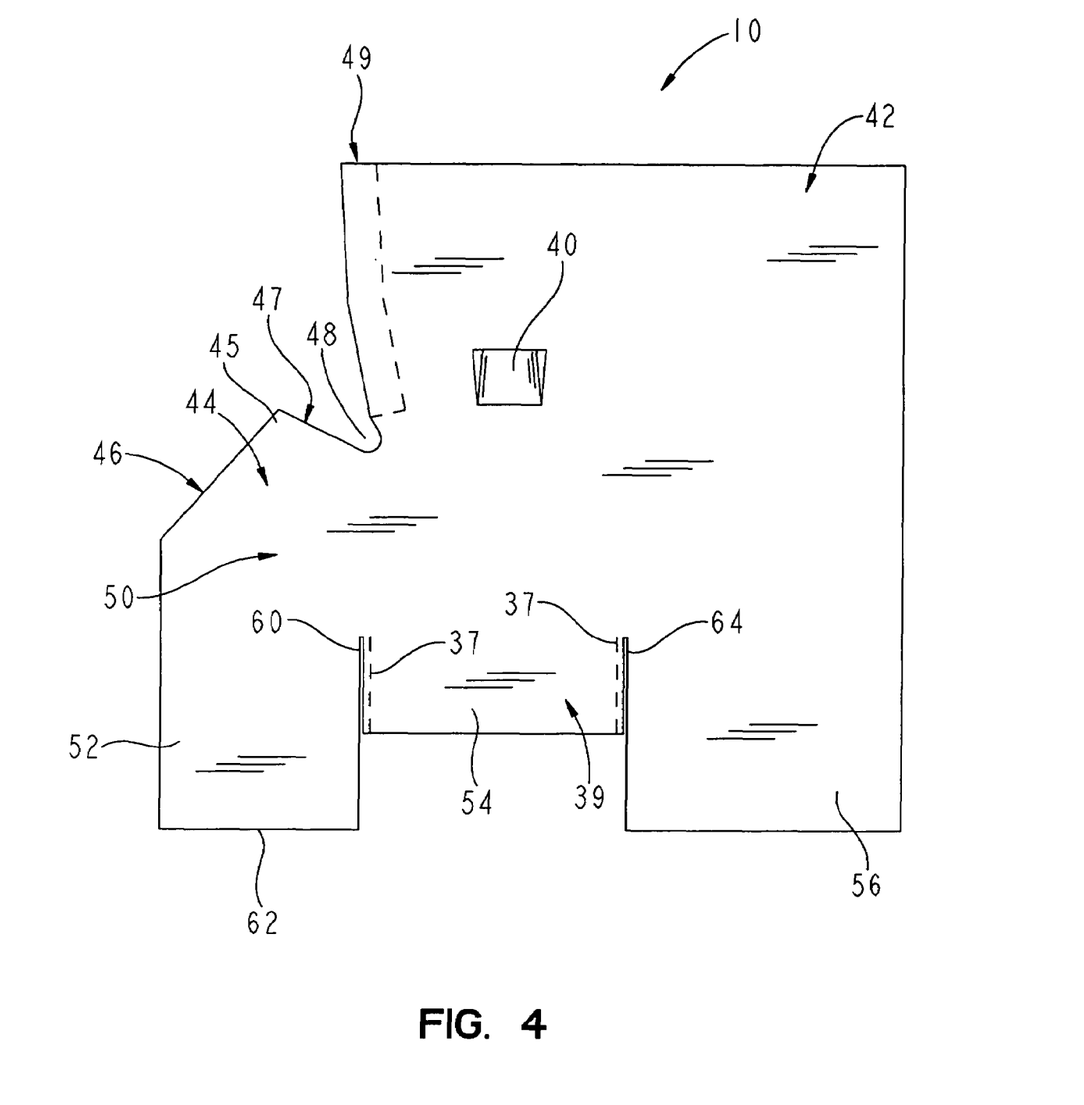
FIG. 4 is a plan view of a cover of the present invention.

Referring now to FIG. 4, the cover 10 may be formed from a single sheet of material. The material used to form the cover 10 may include a flexible cloth-like material made of disposable or incinerable natural or synthetic fibers, woven fibers, as well as plastic or other synthetic sheeting materials. It is preferred that the material used to make the cover 10 is a substantially liquid impervious or liquid repellent material.

The cover 10 may be constructed from a single sheet of material having a generally square or rectangular configuration in which portions of the material are removed. The portions removed define a first portion 42, also seen in FIG. 2, which covers the lower portion of the patient and a portion of the cart. A second portion 44 is formed by removal of material from the substantially rectangular sheet of material to thereby define the second portion 44. The second portion 44 includes a corner 45 defined by an edge 46 and an edge 47 which intersect to form the corner. The edge 46 and edge 47 define a perimeter edge, which may include a triangular shape, a rectangular shape, or other shape to separate the first portion 42 from the second portion 44. The first portion 42 may then be located above the patient while the second portion 44 may be located beneath the patient when in use.

The second portion 44 is tucked underneath the patient's left hip 38, as illustrated in FIG. 2. Material removed at a location 48 thereby defines the first portion 42 and the second portion 44. Once the second portion 44 is placed under the patient's left hip 38, the first portion 42 may be positioned to superimpose or lay over the top of the patient's right thigh, leg and foot. The first portion may be fixed to the patient with an adhesive or adhesive tape which may be attached thereto at a location 49 on the reverse aspect of the drape.

The material used to form the cover includes a third portion 50 which may comprise a third, a half or more of the entire sheet of material, which includes a first segment 52, a second segment 54, and a third segment 56.

The first segment 52 is formed by cutting a line 60, or cutline, substantially perpendicular to an edge 62 of the material. The cutline 60 may be formed by cutting the material along the line 60 or it may be formed by providing perforations to the material which may be torn at a later time to create a cutline of a desired length. A second cutline 64 also formed substantially perpendicular to the edge 62 forms the second segment 54 and the third segment 56. As can be seen in FIG. 2, the first segment 52 lies closest to the head end of the patient support device 16, the second segment 54 lies above or superimposes the barrier 20 and the third segment 56 lies over the edge of the mattress closest to the foot end of the patient supporting device 16. The second segment 54 is folded to form the pocket 39 and fixed at the lines 37.

Figure 5:
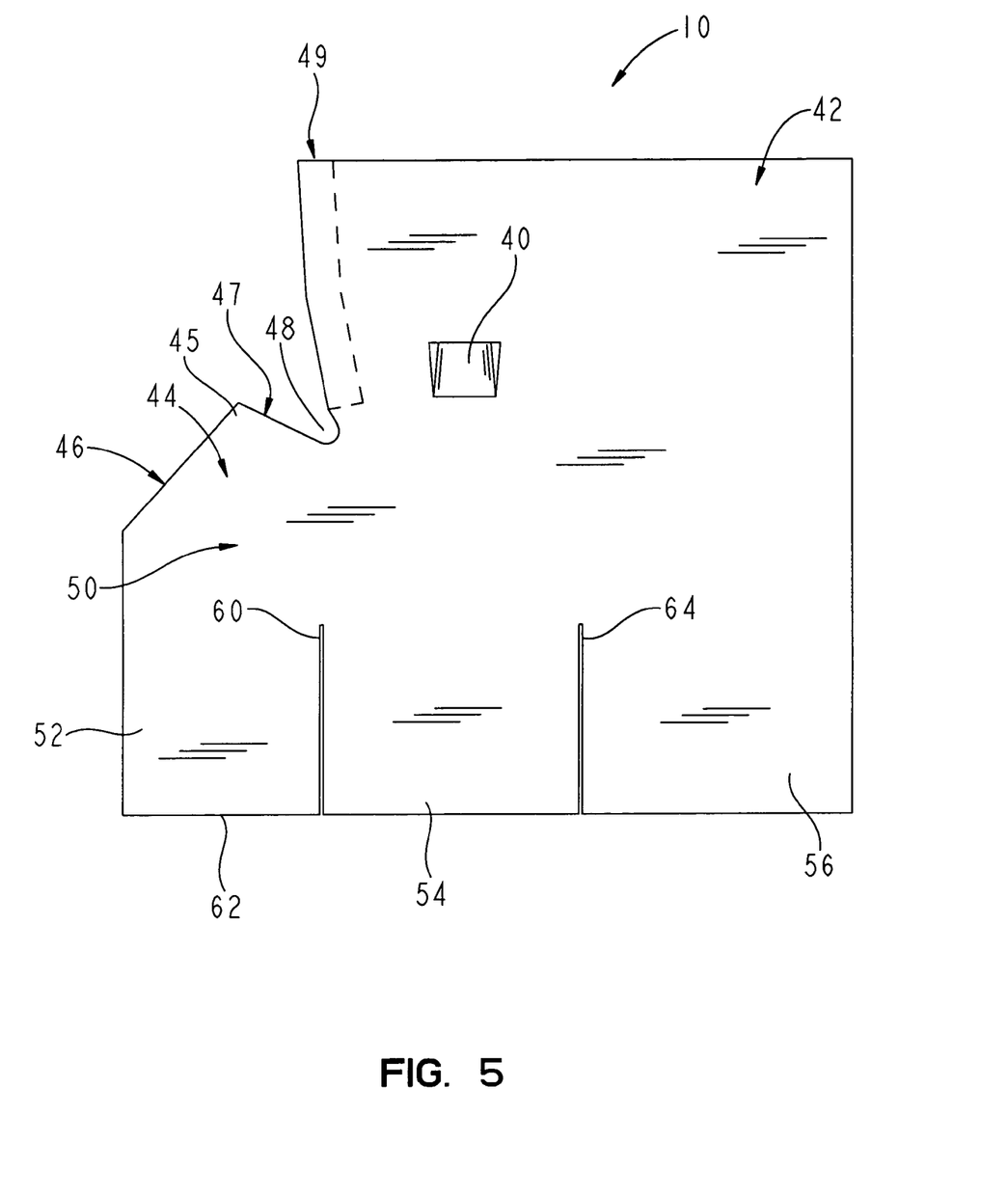
FIG. 5 is a plan view of another embodiment of the cover of the present invention.

FIG. 5 illustrates another embodiment of the cover 10. In this embodiment, the second segment 54 is not folded or fixed so that a pocket is not formed.

Figure 10:
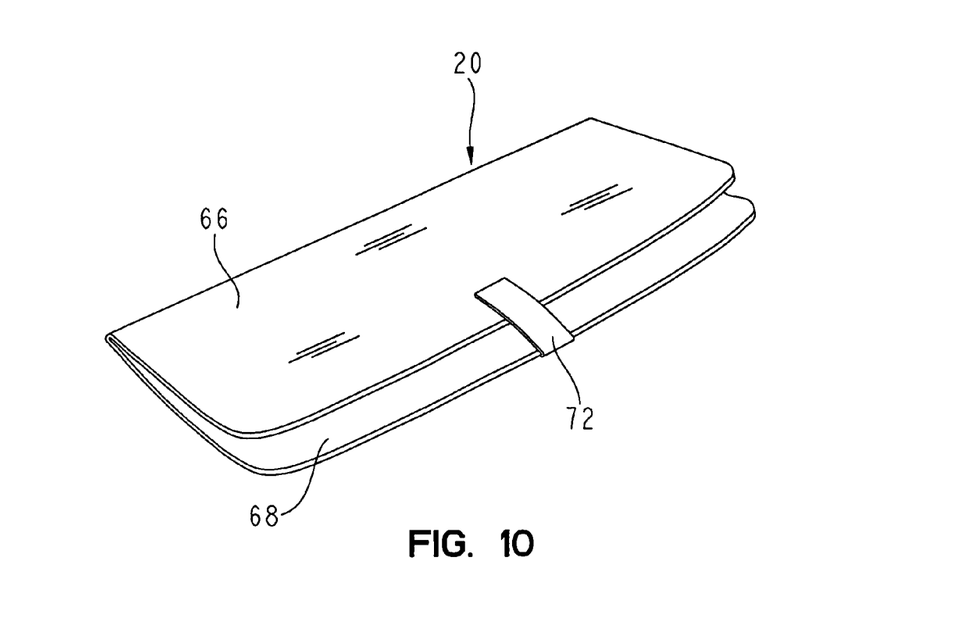
FIG. 10 is a perspective view of the barrier of FIG. 6 in a folded condition.

FIG. 6 is a perspective view of the barrier 20. The barrier 20 includes a first member 66 and a second member 68. Each of the first members 66 and 68 form a substantially flat surface which may be disposed in a substantially perpendicular direction with respect to one another. The first member 66 and the second member 68 are coupled and intersect at a common boundary 70. In a preferred embodiment of the present invention, the barrier 20 is made of a material, such as a plastic material, which may be formed as illustrated to include the first member 66 being substantially perpendicular to the second member 68. The boundary 70 may include a living hinge such that the members 66 and 68 may be folded in a stacked relationship upon one another to a collapsed position or folded position to achieve a substantially parallel orientation for storage as illustrated in FIG. 10. A fastener 72, such as adhesive tape, may hold the members in the substantially parallel configuration until needed.

As illustrated in FIG. 7, the medical procedure drape 8 is initially prepared for use by coupling the barrier 20 to the patient supporting device 16. The second member 68 is inserted in a gap 74 located between the bottom surface of the mattress 18 and the deck 34. It is within the scope of the present invention to couple the barrier 20 to the patient support device 16 with other means or methods as would be understood by those skilled in the art.

The barrier 20 may also be made of other materials such as wood, fiberboard, or cardboard. In addition, the first member 66 and second member 68 need not be the same. Also, the first member 66 could be coupled to projections coupled substantially perpendicularly to the plane of first member 66, where the projections are inserted into the gap 74. In this embodiment, the second member would be absent.

Figure 8:
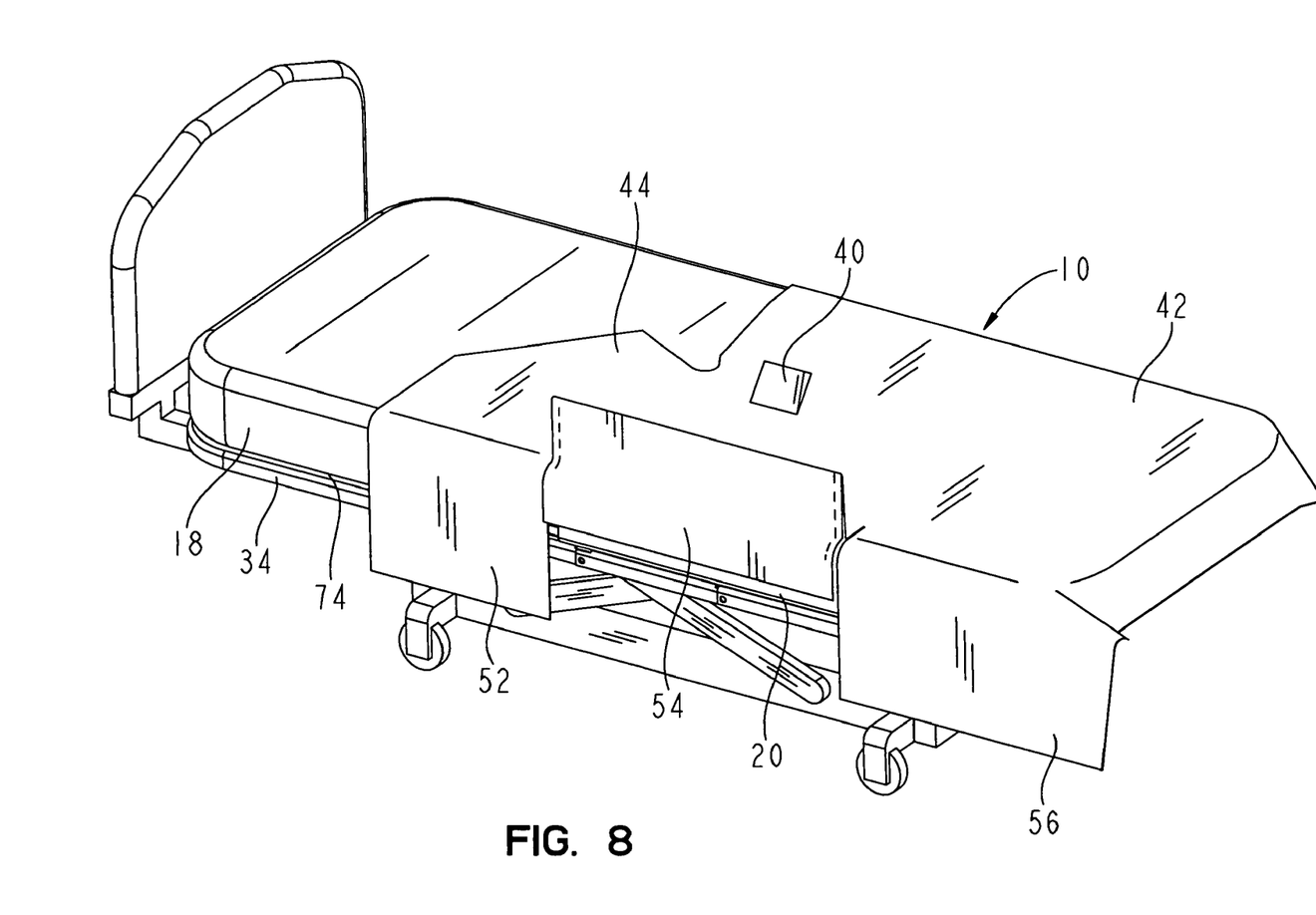
FIG. 8 is a perspective view of the drape of FIG. 4 positioned on the patient support and the barrier of FIG. 7.
Figure 9:
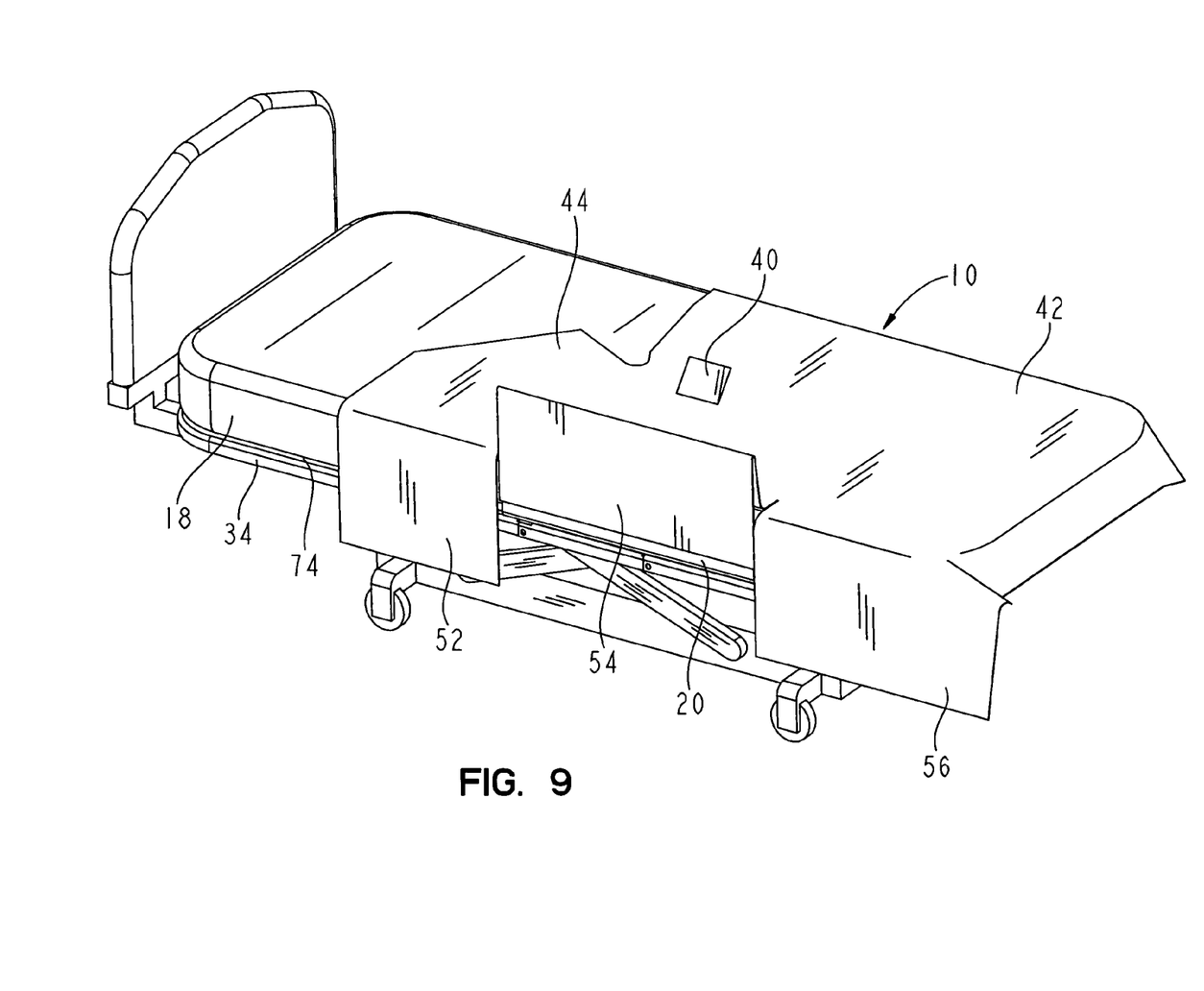
FIG. 9 is a perspective view of the drape of FIG. 5 positioned on the patient support and the barrier of FIG. 7.

Once the barrier 20 is connected to the patient support device 16, the cover 10 is laid upon the mattress 18 and the barrier 20. As illustrated in FIG. 8, the pocket 39 of the cover 10 of FIG. 4 is placed over the first member 66 of the barrier 20. Both the first portion 42 and the second portion 44 lay upon the surface of the mattress 18 while the first segment 52 and the third segment 56 hang downwardly from and generally perpendicular to the surface of the mattress 18. The second segment 54 is supported and held in an elevated position above the surface of the mattress 18 and covers the barrier 20. As illustrated in FIG. 9, the segment 54 of the cover 10 of FIG. 5 hangs over the barrier 20. As previously described when a patient is placed on the mattress 18, the second portion 44 is disposed underneath the patient's left hip 38 and the first portion 42 is disposed on top of the patient. The second segment 54 of the material is located above the surface of the mattress 18 due to the extension of the first member 66 of the barrier 20 above the mattress 18.

Returning now to FIGS. 1 and 2, the colonoscope may be held by the physician 12 in the physician's left hand with the camera, light source, air, and water source at right angles to the patient's cart or supporting surface 16 to the left of the physician. The right hand of the physician is used to control the flexible tube 22, which may be approximately 160 centimeters long. The scope may lie on the cover 10 at an area 80 disposed between the barrier 20 and the patient's leg. The barrier 20 thus holds the scope in position at the area 80 whereby the space may accommodate the full length of the endoscope extending towards the foot of the supporting surface and then returning back towards the physician's right hand which controls the actuation of the device.

The colonoscope 24 is manipulated into and through the large intestine of the patient with the operator's right hand. The barrier 20, having a portion thereof located above the surface of the mattress 18, serves a purpose of containing the scope within the area 80 between the barrier 20 and the patient 14. Consequently, the scope may be prevented from falling off of the patient cart as well as from contacting the physician 12. The barrier 20 may also allow the patient to be positioned more closely to the edge of the supporting surface so that the physician's need to lean over or to reach a long distance to manipulate the instrument is reduced or eliminated. By enabling physician control of the instrument through the location of the barrier, the procedure may be completed in a safe and quick manner thereby reducing fatigue.

Upon withdrawal of the scope from the patient, the flexible tube 22 may be placed in the area 80. Once placed in the area 80, the remainder of the scope is withdrawn, and placed on the cover 10, thereby reducing or eliminating contamination of the patient support surface. Once the examination is completed, the scope is completely withdrawn and then may be removed from the location of the procedure or procedure field onto a separate table. The patient may then be cleansed and the medical procedure drape removed in such a way that no contamination remains on the patient, the patient supporting device, the endoscopy staff, or the endoscopy suite. The patient is then transferred to a holding area for monitoring until fully recovered. The cover and the barrier may then be folded appropriately to include any waste in the interior of the cover. The cover and barrier 20 may then be disposed of either through incineration or other means.

Figure 11:
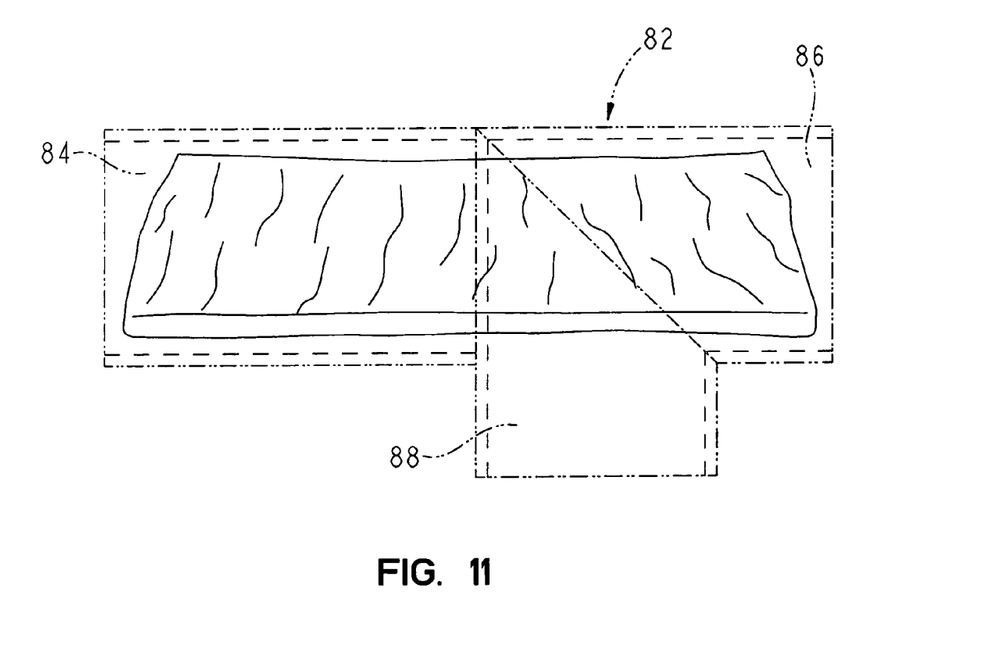
FIG. 11 is a perspective view of the cover of FIG. 4 in a folded condition located adjacent the barrier of FIG. 10 and partially enclosed in a package.

The medical procedure drape may be provided to a hospital or physician as a kit 82, illustrated in FIG. 11. The kit 82 includes the folded barrier 20 of FIG. 10 and the cover 10. The cover 10 may be folded and placed next to the barrier 20 or the cover 10 may be wrapped around the folded barrier 20. The package 84 may also be formed around the barrier/cover combination. A first sheet 86 and a second sheet 88 are bonded or held together by an adhesive to form the package 82. When required, the kit is opened by removing one sheet from another to allow the barrier/cover combination to be used.

While this invention has been described with specific embodiments thereof, alternatives, modifications and variations may be apparent to those skilled in the art. For instance it is within the scope of the present invention to make the cover from more than one piece or sheet of material. In addition, the barrier 20 may be adhered to or fixed to the segment 54 or to the pocket 39 such that when placed at the patient support, the combination cover and barrier cooperate as a single unit for placement. Accordingly, it is intended to embrace all such alternatives, modifications and variations that fall within the spirit and broad scope of this appended claims.

What is claimed is:

1. A medical procedure drape, for use during a medical procedure performed on a patient supported by a patient support surface disposed on a frame, comprising:
   a cover including a first portion to superimpose one part of a patient, a second portion to subtend another part of the patient, an edge, a first cutline, and a second cutline, the first cutline and the second cutline extending from the edge of the cover and defining a first segment, a second segment, and a third segment, the second segment being disposed between the first segment and the third segment, the second segment having a width defined by the first cutline and the second cutline, each of the cutlines defining a complete separation of the cover along the length of the cutline, each of the cutlines being located between adjacent segments prior to the performance of the medical procedure; and
   a barrier, including a first member coupled to a second member, the first member having a width sufficient to support the second segment of the cover, the first member disposed adjacent the second segment of the cover to define a substantially contiguous surface between the first member and the patient to confine the location of a device used during the medical procedure, the first member and supported second segment of the cover extending above the patient support surface.

2. The medical procedure drape of claim 1, further comprising a holder, coupled to the cover, the holder being adapted to hold an assisting device.

3. The medical procedure drape of claim 1, wherein the second member includes a storage position disposed substantially parallel with the first member and having a use position disposed substantially perpendicular to the first member.

4. The medical procedure drape of claim 1, wherein the barrier comprises a plastic material and a living hinge to couple the first member to the second member to enable the first member to be disposed substantially parallel to the second member.

5. The medical procedure drape of claim 4, wherein the second member is substantially planar to provide for the location thereof between the patient support surface and the frame, the first member being substantially planar and upstanding with respect to the second member to define a space between the first member and the patient, the space defining an area to confine a device used during the medical procedure, and the first member including a height sufficient to confine the device between the patient and the first member.

6. The medical procedure drape of claim 1, wherein the barrier and cover comprise an incinerable material.

7. The medical procedure drape of claim 1, wherein the width of the barrier is sufficient to support greater than half the width of the second segment.

8. The medical procedure drape of claim 1, wherein the width of the barrier is sufficient to support a substantial portion of the width of the second segment.

9. The medical procedure drape of claim 1, wherein the cover includes a space disposed between an edge of the first portion of the cover and an edge of the second portion of the cover when the first portion and second portion are laid flat and do not overlap such that the edge of the first portion is non-parallel to the edge of the second portion.

10. The medical procedure drape of claim 1, wherein the cover comprises a unitary flexible material.

11. The medical procedure drape of claim 1, wherein the cover includes an adhesive coupled to the first portion, to fix the first portion to the patient.

12. A medical procedure drape, for use during an endoscopic procedure performed on a patient supported by a patient support surface, comprising:
   a cover including a first portion to superimpose one part of a patient, an adhesive coupled to the first portion to fix the first portion to the patient, a second portion to subtend another part of the patient, an edge, a first cutline, and a second cutline, the first cutline and the second cutline extending from the edge of the cover and defining a first segment, a second segment, and a third segment, the second segment being disposed between the first segment and the third segment, the second segment having a width defined by the first cutline and the second cutline, each of the cutlines defining a complete separation of the cover along the length of the cutline, each of the cutlines being located between adjacent segments prior to the performance of the endoscopic procedure, and wherein an edge of the first portion of the cover and an edge of the second portion of the cover define a space having non-parallel sides when the first portion and second portion are laid flat and do not overlap; and a barrier, including a first member, a second member, and a living hinge coupled to the first member and to the second member to enable the first member to be disposed substantially parallel to the second member in a storage position and substantially perpendicular to the second member in a use position, the first member having a width sufficient to support a portion of the width of the second segment of the cover, the first member disposed adjacent the second segment of the cover to define a substantially horizontal surface between the first member and the patient to confine a device used during the endoscopic procedure, the first member and supported segment of the cover extending above the patient support surface.

13. The medical procedure drape of claim 12 wherein the first member and second member of the barrier are substantially planar and include substantially the same width.

14. The medical procedure drape of claim 13, wherein the first member includes a width sufficient to support a substantial portion of the width of the second segment of the cover.

15. The medical procedure drape of claim 12, wherein the second segment is coupled to the first member of the barrier, and the first member includes a height sufficient to confine the device on the cover between the patient and the first member.

* * * * *